(12) United States Patent
Miller et al.

(10) Patent No.: US 10,537,414 B2
(45) Date of Patent: Jan. 21, 2020

(54) PERSONAL CARE DEVICE ACTUATOR WITH RATTLE MITIGATION

(71) Applicant: KONINKLIJKE PHILIPS N.V., Eindhoven (NL)

(72) Inventors: Kevin Arnold Miller, Bellevue, WA (US); Wolter F. Benning, Seattle, WA (US); Gregory Russ Goddard, Kenmore, WA (US); Evert Alle Helfrich, Seattle, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 185 days.

(21) Appl. No.: 15/536,471

(22) PCT Filed: Dec. 15, 2015

(86) PCT No.: PCT/IB2015/059606
§ 371 (c)(1),
(2) Date: Jun. 15, 2017

(87) PCT Pub. No.: WO2016/103105
PCT Pub. Date: Jun. 30, 2016

(65) Prior Publication Data
US 2017/0367802 A1  Dec. 28, 2017

Related U.S. Application Data

(60) Provisional application No. 62/096,055, filed on Dec. 23, 2014.

(51) Int. Cl.
*H02K 7/06* (2006.01)
*A61C 17/34* (2006.01)
(Continued)

(52) U.S. Cl.
CPC ...... *A61C 17/3418* (2013.01); *A61C 17/3445* (2013.01); *H02K 7/09* (2013.01); *H02K 33/18* (2013.01); *H02K 7/083* (2013.01)

(58) Field of Classification Search
CPC .. A61C 17/3418; A61C 17/3445; H02K 7/09; H02K 7/083; H02K 7/06; H02K 7/061;
(Continued)

(56) References Cited

U.S. PATENT DOCUMENTS

2009/0070948 A1\* 3/2009 Bax .................. A61C 17/22
15/22.2
2013/0207575 A1 8/2013 Bax et al.
(Continued)

FOREIGN PATENT DOCUMENTS

| CN | 201726240 | 1/2011 |
| JP | 2013123305 A | 6/2013 |
| WO | 2012042427 A2 | 4/2012 |

*Primary Examiner* — Michael Andrews

(57) ABSTRACT

An actuator (12) for a personal care appliance (10) having an eccentric core (21) to preload the actuator (12) to prevent rattling caused by detrimental reactionary forces. The eccentric core (21) includes a pole assembly (24) radially extending from a spindle (22) having at least a first set (25-1) and a second set (25-2) of pole members. The first set (25-1) has a greater length as measured from the center of the spindle (22) than the second set (24-2), reducing the magnet gap on one side of the spindle (22) to create an eccentric core and preload the actuator (12). Alternatively, the preload can be mechanically created by a set of bearings (28) disposed within housing (18) of the actuator (12), where the bearings (28) have a centerline (A3) offset from the principal axis (A1) of the housing (18).

8 Claims, 4 Drawing Sheets

(51) Int. Cl.
*H02K 33/18* (2006.01)
*H02K 7/09* (2006.01)
*H02K 7/08* (2006.01)

(58) Field of Classification Search
CPC ........ H02K 7/063; H02K 7/065; H02K 7/075; H02K 1/17; H02K 1/24; H02K 1/246; H02K 33/18; H02K 33/02; H02K 35/06
USPC ........... 310/216.001, 12.24, 37, 38, 216.074, 310/216.096, 216.097
See application file for complete search history.

(56) References Cited

U.S. PATENT DOCUMENTS

| | | |
|---|---|---|
| 2014/0015346 A1 | 1/2014 | Schober et al. |
| 2016/0324610 A1* | 11/2016 | Bax ........................ A61C 17/34 |
| 2016/0324611 A1* | 11/2016 | Bosman ............. A61C 17/3418 |
| 2017/0100224 A1* | 4/2017 | Wills ................... A61C 15/047 |

* cited by examiner

PERSONAL CARE DEVICE ACTUATOR WITH RATTLE MITIGATION

CROSS-REFERENCE TO PRIOR APPLICATIONS

This application is the U.S. National Phase application under 35 U.S.C. § 371 of International Application No. PCT/IB2015/059606 filed on Dec. 15, 2015, which claims the benefit of U.S. Provisional Patent Application No. 62/096,055, filed on Dec. 23, 2014. These applications are hereby incorporated by reference herein.

FIELD OF THE INVENTION

The present disclosure is directed generally to improved drive systems for a personal care appliance, such as a power tooth brush, and more particularly, to drive systems including an actuator with rattle mitigation.

BACKGROUND

Electric personal care devices, such as electric toothbrushes, are a growing market, and produced by a large number of manufacturers. While these personal care devices may vary in their operations, most contain an electric motor adapted to rotate a brush head in a reciprocating axial and/or tangential motion.

In operation, the electric motor in these personal care devices may be subjected to varied unwanted, unintended and/or otherwise detrimental reactionary forces. These forces can impact the effectiveness of the personal care devices, and can negatively impact a user's experience with the device. For example, an electric toothbrush may be subjected to a detrimental reactionary force that arises from friction between the user's teeth and rotating bristles of the brush head of an electric toothbrush, as the bristles reciprocate back and forth across the user's teeth. As another example, if the center of mass of the brush head is misaligned with the axis of rotation of the electric toothbrush device, an unwanted reactionary force may arise from drive motion of the motor on the brush. These detrimental forces can manifest as tangential reciprocating loads on the electric motor disposed within the electric toothbrush.

These forces are considered detrimental as they may cause unwanted behavior from the electric motor. For example, most electric motors have a shaft or spindle that rotates. The shaft is mounted in the bearings within the electric motor. If there is any clearance between the bearings and the shaft of the electric motor, these detrimental forces could cause the shaft come off the surface of the bearings and then impact the bearings, resulting in an unpleasant rattle and unnecessary wear on the shaft and bearings.

Accordingly, there is a need in the art for an electric motor that will not rattle or experience unnecessary wear due to these detrimental forces.

SUMMARY OF THE INVENTION

The present disclosure is directed to inventive apparatus for inducing a preload on an actuator used in a personal care appliance. Various embodiments and implementations herein are directed to an apparatus to induce a preload on an actuator in a personal care appliance by implementing an asymmetrical magnet gap between a core, comprising a spindle with radially extending pole members, and magnets disposed about the interior of a housing. Other embodiments are directed to an eccentric core, which is defined herein as a spindle with pole members of varying lengths radially extending from the spindle. Further embodiments are directed to an apparatus to induce a mechanical preload on an actuator by disposing a spindle with pole members within bearings with a centerline offset from the housing centerline.

Using the various embodiments and implementations herein, rattling of an actuator that results from detrimental reactionary forces may be substantially improved by inducing a preload.

One example of an electric toothbrush device using an actuator is a Sonicare® device available from Koninklijke Philips Electronics N.V. The oral care device is based upon an actuator with a reciprocating brush head, with bristles to provide an effective cleaning of a user's teeth. The oral care device is subjected to detrimental reactionary forces from, among others, the reaction force on the brush head from the user's teeth that could cause the spindle in the actuator to come off and then impact the bearing within the device. In the embodiments disclosed herein, an asymmetrical magnet gap between a core and magnets disposed about the interior of the housing induces a preload effective to press the core into the bearings such that it does not come off the bearings as a result of detrimental reactionary forces. A further embodiment is directed to an eccentric core, a spindle with pole members of varying lengths radially extending from the spindle, which induces a preload effective to mitigate the effect of any detrimental reactionary forces. In other embodiments, configuring a spindle disposed within bearings with a centerline offset from the housing centerline further induces a preload effective to mitigate the effects of any detrimental reactionary forces.

Generally in one aspect, an actuator for a personal care appliance is provided and includes: a housing having an inner surface and a principal axis extending longitudinally through the center of the housing, and having sequence of more than one magnet, disposed along the inner surface of the housing; and an eccentric core, including: a spindle of magnetizable material extending along a secondary axis, and a first pole assembly, arranged in a radial configuration about the spindle, and including a first set of pole members including at least one pole member extending radially at least a first average distance from the spindle, and a second set of pole members including at least one pole member extending radially a second average distance from the spindle, where the length of the first average distance is greater than the length of the second average distance, such that the spindle is subjected to a bias force in a bias direction, radially from the principal axis, whereby the secondary axis is offset from the principal axis.

According to an embodiment, the first set of pole members include more pole members that the second set of pole members.

According to an embodiment, the first set of pole members includes three consecutive pole members, and the second set of pole members includes two consecutive pole members.

According to an embodiment, the first set further includes at least one pole member extending radially further than the remainder of the pole members in the first set.

According to an embodiment, the actuator further includes an output mounting shaft coupled to the housing and exhibiting a force in a radial direction upon the spindle when in use, wherein the bias direction is substantially opposed to the radial direction.

According to an embodiment, the actuator further includes an output mounting shaft coupled to the housing and exhibiting a force in a radial direction upon the spindle when in use, wherein the bias direction is in substantially the same as the radial direction.

According to an embodiment, the bias force is generally about 5 Newtons.

According to an embodiment, the eccentric core further includes: a second pole assembly, arranged in a radial configuration about the spindle, and including a third set of pole members including at least one pole member extending radially a third average distance from the spindle, and a fourth set of pole members including at least one pole member extending radially a fourth average distance from the spindle, wherein the length of the third average distance is greater than the length of the fourth average distance.

In another aspect, an actuator for a personal care appliance includes: a housing having an inner surface and a principal axis extending longitudinally through the center of the housing, and having sequence of more than one magnet, disposed along the inner surface of the housing; a set of bearings disposed within housing, wherein the bearings have a centerline offset from the principal axis; and a spindle, having a pole assembly, arranged in a radial configuration about the spindle, wherein the spindle is disposed within the bearings, along a secondary axis offset from the principal axis.

According to an embodiment, the centerline is the same as the secondary axis.

According to an embodiment, the centerline is the different as compared to the secondary axis.

According to an embodiment, the pole assembly further includes a plurality of pole members of substantially the same length.

According to an embodiment, the bearings are common bearings. According to an embodiment, the common bearings are bushing bearings.

In a further aspect, an actuator for a personal care appliance includes: a housing having an inner surface and a principal axis extending longitudinally through the center of the housing, and having sequence of more than one magnet, disposed along the inner surface of the housing; and a spindle disposed within the housing and having a pole assembly arranged in a radial configuration about the spindle, wherein the spindle and pole assembly are configured, structured, and/or positioned to form an asymmetrical magnet gap between the pole assembly and the magnets, such that the spindle and pole assembly are subjected to a bias force.

According to an embodiment, the actuator further includes a set of bearings having no more than two bearings.

These and other aspects of the invention will be apparent from and elucidated with reference to the embodiment(s) described hereinafter.

BRIEF DESCRIPTION OF THE DRAWINGS

In the drawings, like reference characters generally refer to the same parts throughout the different views. Also, the drawings are not necessarily to scale, emphasis instead generally being placed upon illustrating the principles of the invention.

DETAILED DESCRIPTION OF EMBODIMENTS

The present disclosure describes various embodiments of inducing a preload on an actuator used in a personal care appliance. More generally, Applicants have recognized and appreciated that it would be beneficial to induce a preload on an actuator in a personal care appliance by implementing an asymmetrical magnet gap between a core, comprised of a spindle and a plurality of radially extending pole members, and magnets disposed about the interior of a housing. For example, the rattling in an electric toothbrush, created by the detrimental reactionary force from the bristles on the user's teeth may be substantially improved by inducing such a preload. Applicants have also recognized that it would be beneficial to induce a preload on an actuator in a personal care appliance with an eccentric core, or by disposing a core within bearings having a centerline offset from the housing centerline. This is true for any tangential detrimental reactionary force acting upon the actuator sufficient to force the actuator off its bearings and induce a rattle.

Embodiments disclosed herein provide an actuator in a personal care appliance with a preload induced by an asymmetrical magnet gap. Other embodiments are directed to an apparatus with a preload induced by an eccentric core. Further embodiments are directed to an apparatus to induce a preload on an actuator by disposing a core within bearings having a centerline offset form the housing centerline.

A particular goal of utilization of the embodiments of the present disclosure is the ability of the actuator with rattle mitigation (in view of the induced preload) to be used in any personal care device. Another goal is to improve a user's experience by mitigating the rattle in the handle of a personal care device per the implementation of the induced preload.

In view of the foregoing, various embodiments and implementations are directed to an actuator that includes a core positioned, configured, and/or structured to induce a preload on the actuator sufficient to mitigate any rattling that may occur because of detrimental forces acting on the core. In these embodiments, the core may further include a forward and rear pole assembly, both exhibiting the same or different eccentricity to further preload the actuator to counteract the detrimental forces.

Figure 1:
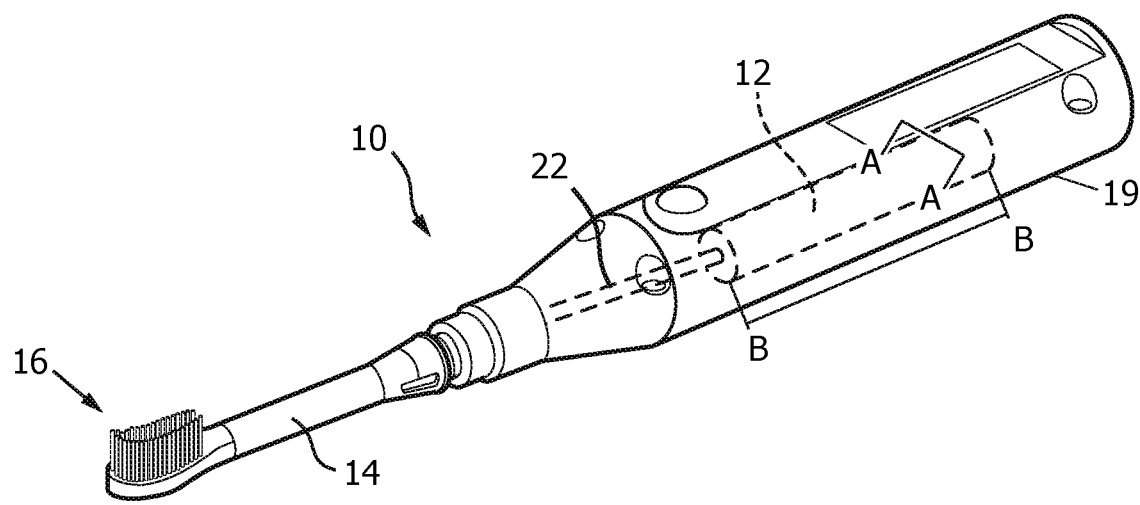
FIG. 1 is a perspective schematic of a personal care appliance.

Referring to FIG. 1, in one embodiment, a personal care appliance 10, including an actuator 12, generally disposed within a handle 19 of the personal care appliance 10 is provided. The personal care appliance is adapted to drive an output mounting shaft 14 via a spindle 22. The output mounting shaft 14 may terminate in a work piece 16, such as a brush head, or other dental appliance.

Figure 2:
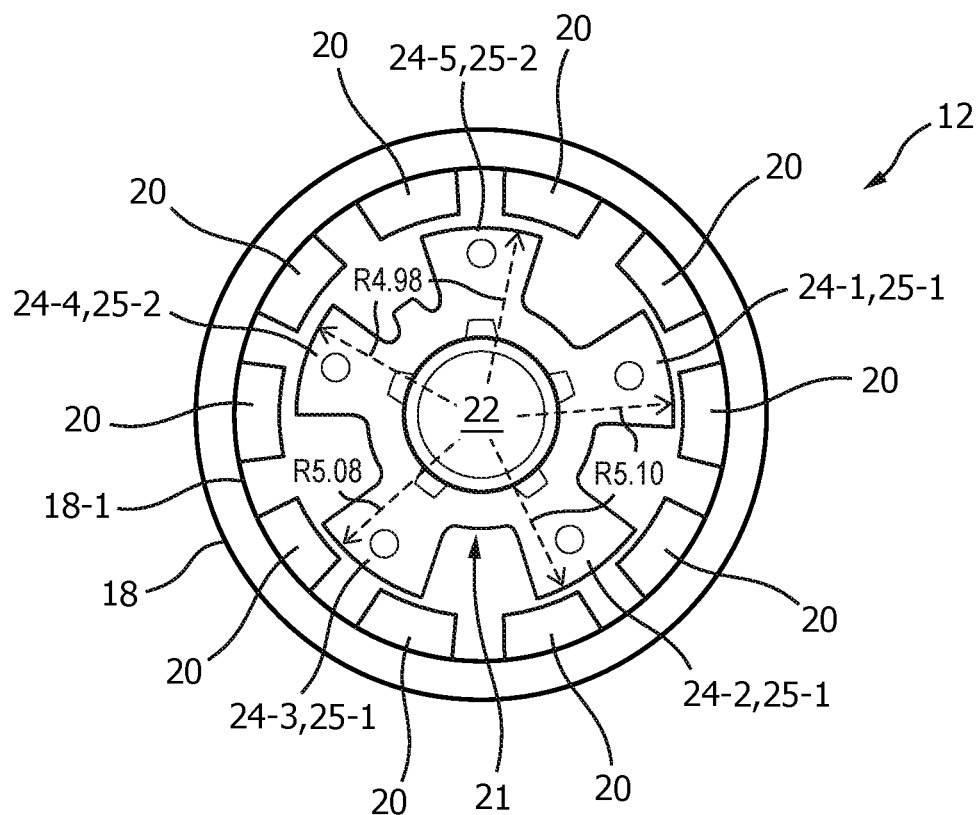
FIG. 2 is a cross-sectional view of a personal care appliance taken along "A-A" of FIG. 1 according to one embodiment.
Figure 3:
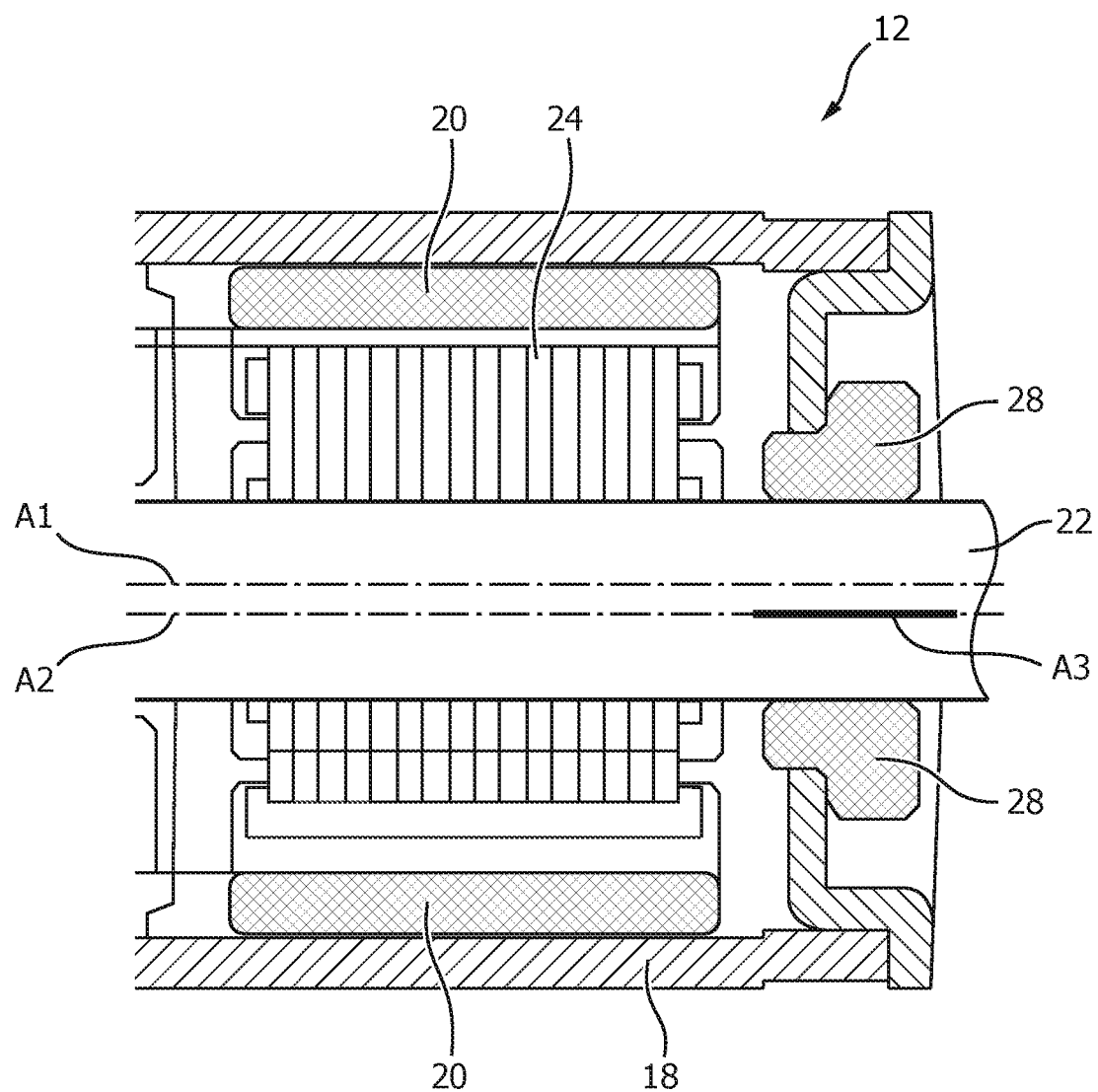
FIG. 3 is a cross-sectional view of a personal care appliance taken along "B-B" of FIG. 1 according to an embodiment.

Referring to FIG. 2, in one embodiment, there is shown a cross sectional view of the interior of the actuator 12 as sectioned along "A-A" from FIG. 1. Actuator 12 generally includes a housing 18, having a principal axis A1 (as shown in FIG. 3) extending longitudinally through the center of housing 18, and magnets 20 disposed along the inner surface of the housing 18-1. Magnets 20 may include North (N) and South (S) magnets alternately and evenly disposed about the inner surface 18-1 of the housing 18. However, one of ordinary skill in the art will recognize that the magnets may also be grouped N-S magnets. Furthermore, the magnets 20 may, in alternative embodiments, be spaced sporadically about the inner surface, and may not alternate between N and S, but may be arranged in consecutive pairings such as, N-N, S-S, N-N-N, etc. Persons of ordinary skill in the art will understand that magnets 20 of any suitable strength can be used. For example, in certain embodiments, magnet grades of N40-N50 may be used.

Furthermore, actuator 12 houses a core 21, including: a spindle 22 and a first pole assembly 24-n of magnetizable material, extending radially from the spindle 22. For the purposes of this disclosure, "magnetizable material" is defined to mean any ferromagnetic, paramagnetic, or superparamagnetic, material. In one embodiment, the spindle 22 is driven in a tangential, reciprocating motion; however, one of ordinary skill in the art will recognize that the actuator may be configured drive the spindle in an axial motion.

According to an embodiment, the spindle 22 and pole assembly 24 are disposed, structured, and configured within the housing to form an asymmetrical magnet gap between the pole assembly 24 and the magnets 20, such that the additional force of the magnet(s) on the nearest portion of the pole assembly 24 induces a preload on the spindle and pole assembly. Other non-limiting embodiments which create an asymmetrical magnet gap are described in detail below, including the eccentric core 21, and bearings disposed within the housing having a centerline offset from the housing centerline.

According to one embodiment, the core 21 shown in FIG. 2 is an eccentric core 21, which includes first pole assembly 24 with pole members of varying lengths, and is useful to induce a preload sufficient to overcome rattling caused by detrimental reactionary forces (as described above). In an exemplary embodiment, first pole assembly 24 is divided into at least two sets of pole members 25-1, 25-2. The pole members of each set 25-1, 25-2, preferably have an average length (measured from the center of spindle 22 to the farthest radial edge of a particular pole member), such that the average length of pole members in set 25-1 is greater than the average length of pole members in set 25-2. In other words, each of the pole members 25-1 preferably has a length (e.g., 5.08 mm) larger than the length of each pole member in set 25-2 (e.g., 4.98 mm) (although this is not necessary, as long as the average length is greater).

For example, as shown in FIG. 2, the eccentric core 21 can have five (5) pole members, of which, three consecutive pole members, 24-1, 24-2, 24-3, in set 25-1, have an average length greater than the average length of the remaining pole members, 24-4, 24-5, in set 25-2. Because set 25-1 has a larger average length than the average length of set 25-2, the pole members of set 25-1 are closer to the magnets 20 on the inner surface 18-1 of the housing (0.22 mm space between pole members in set 25-1 vs. 0.32 mm space between pole members in set 25-2). This closer proximity of the pole members of set 25-1 to the magnets 20 will cause the pole members of set 25-1 to be subjected to a greater magnetic attraction to magnets 20, drawing the core to the magnets on the side of the spindle including the pole members of set 25-1, "preloading" the core and creating an asymmetrical magnet gap.

In one embodiment, the three pole members 24-1, 24-2, 24-3, in set 25-1, may each have the same length of 5.08 mm, while the remaining two 24-4, 24-5, may have a radius of 4.98 mm. However one of ordinary skill in the art will readily recognize that other lengths may be used for pole members of first pole assembly 24, creating different magnet gaps and different preloads. For example, pole members in set 25-1 may have a length of 5.05 mm and the pole members in set 25-2 may have a length of 4.98 mm, creating a smaller preload than the above-described embodiment.

One of ordinary skill will recognize that the eccentric core 21 may have any number of pole members of first pole assembly 24. For example, eccentric core 21 may have only two pole members, with one that is longer than the other. In another example, eccentric core 21 may have seven pole members, four of which are longer than the other three. Alternatively, the eccentric core 21 may have six pole members, three of which are longer than the other three. For any even number of pole members, in an exemplary embodiment, the ratio of longer to shorter members may be one to one. For any odd number of pole members, in an exemplary embodiment, the ratio of longer to shorter members may be one greater than one to one (for example, with three pole members, two would be longer than the other one; with five pole members, three would be longer than the other two; with seven pole members, four would be longer than the other three). However, one of ordinary skill will recognize that pole assembly 24 may have any ratio of pole longer to shorter members. For example, with seven pole members, three may be longer, and four may be shorter, without departing from the scope of the invention.

Furthermore, one of ordinary skill will recognize that each pole member in a set 25-1/25-2 may have may a length different from other pole members. For example, in set 25-1, the center pole member 24-2, may have a larger length than the remaining pole members in 25-1. The length of the individual pole members can be selected according to varying preloading needs.

Referring to FIG. 3, in one embodiment, there is shown a cross sectional view of the interior of the actuator 12 as sectioned along "B-B" from FIG. 1. This embodiment shows spindle 22 as it is disposed within housing 18, centered on secondary axis A2, offset radially from principal axis A1, as a result of the biasing caused by eccentric core 21 (shown in FIG. 2).

Figure 4:
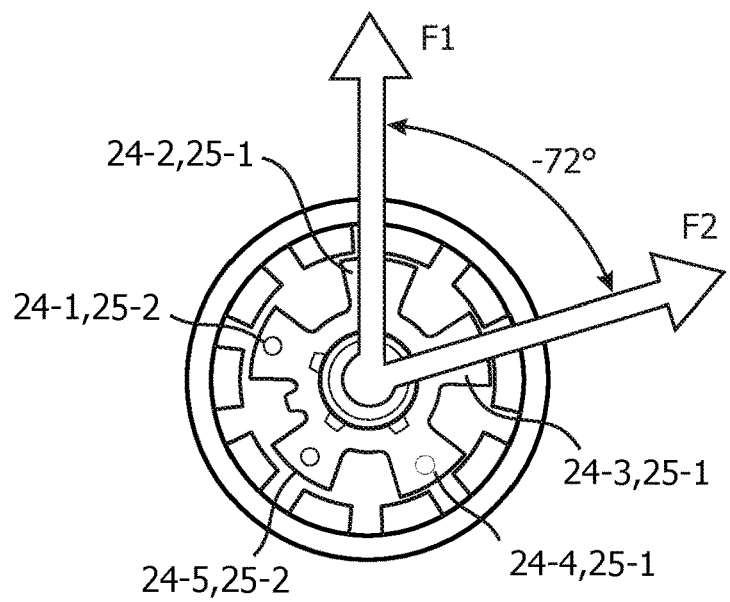
FIG. 4 is a cross-sectional view of a personal care appliance taken along "A-A" of FIG. 1 according to another embodiment.

As described above with respect to FIG. 1, the personal care appliance 10 may be adapted for the spindle 22 to drive an output mounting shaft 14. Output mounting shaft 14, when in use against a user's teeth and gums, may exhibit a radial force on the spindle 22. This force may bias the spindle 22 against the housing 18, effectively creating a "brush load." To account for this brush load during use, it may be beneficial to orient pole members of set 25-1 such that the preload is induced in a direction substantially the same as the radial force. FIG. 4 shows a cross-section of actuator, according to one embodiment, depicting vectors F1 and F2, representing both the magnitude and direction of the brush load force and preload force, respectively. If the brush head generates a radial force F1, for a five pole-member eccentric core, set 25-1 may have to be oriented in substantially the same direction, to generate a preload at a 72° angle to F1. This configuration will cause the preload force F2 and the brush load force F1 to add to form an effectively larger force in a direction between F1 and F2. This configuration may be optimal given the force of F1, F2 and the magnitude of any detrimental reactionary forces. Similarly, the pole members with larger lengths may be selected such that the angle between F1 and F2 may be 0°. However, given the magnitude of the brush load force F1 and the preload force F2, if F1 and F2 are substantially in the same direction (for the purposes of this disclosure, "substantially the same direction" may mean any angle less than 90°), may create too much friction between the eccentric core and the bearings.

Figure 5:
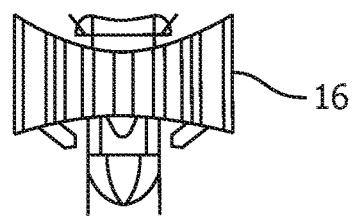
FIG. 5 is a cross-sectional view of a personal care appliance taken along "A-A" of FIG. 1 according to yet another embodiment.
Figure 5:
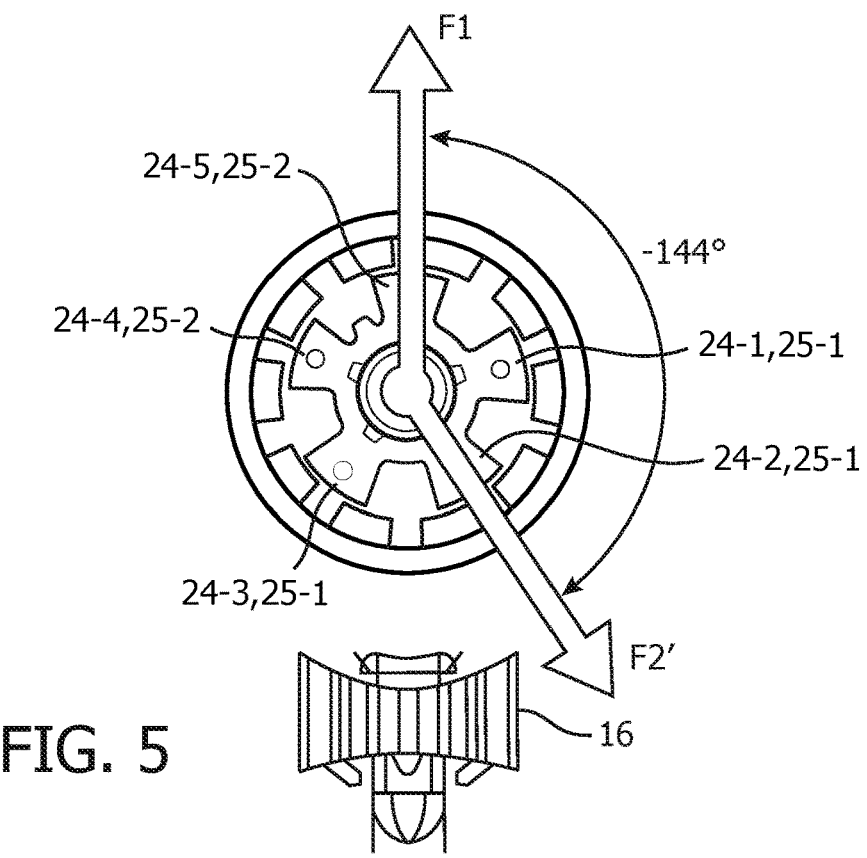

As a result, it may be beneficial to select pole members to create a preload force F2' in a direction substantially opposed to the brush load F1. For the purposes of this disclosure, "direction substantially opposed to" is defined as greater than or equal to 90° and less than or equal to 270°. For example, set 25-1 may be oriented away from F1, shown in FIG. 5. In this embodiment, F1 and F2' are separated by a 144° angle. Given the magnitude of F1, F2, and the reactionary forces, this may result in a preload force that prevents the rattling of the motor, but does not add with F1 in a manner that creates too much friction between the bearing 28 and the eccentric core 21. One of ordinary skill in the art will recognize that any number of angles may be chosen between F1 and F2/F2', including 90° and 180°. The angle may be selected according to a number of factors including, but not limited to: number of magnets 20, number of pole members, length of pole members, gap between magnets 20 and pole members, magnitude of the preload force F2/F2', magnitude of the brush load force F1, magnitude of the reactionary forces, the friction generated between the eccentric core 21 and the bearings for a chosen angle, etc.

Figure 6:
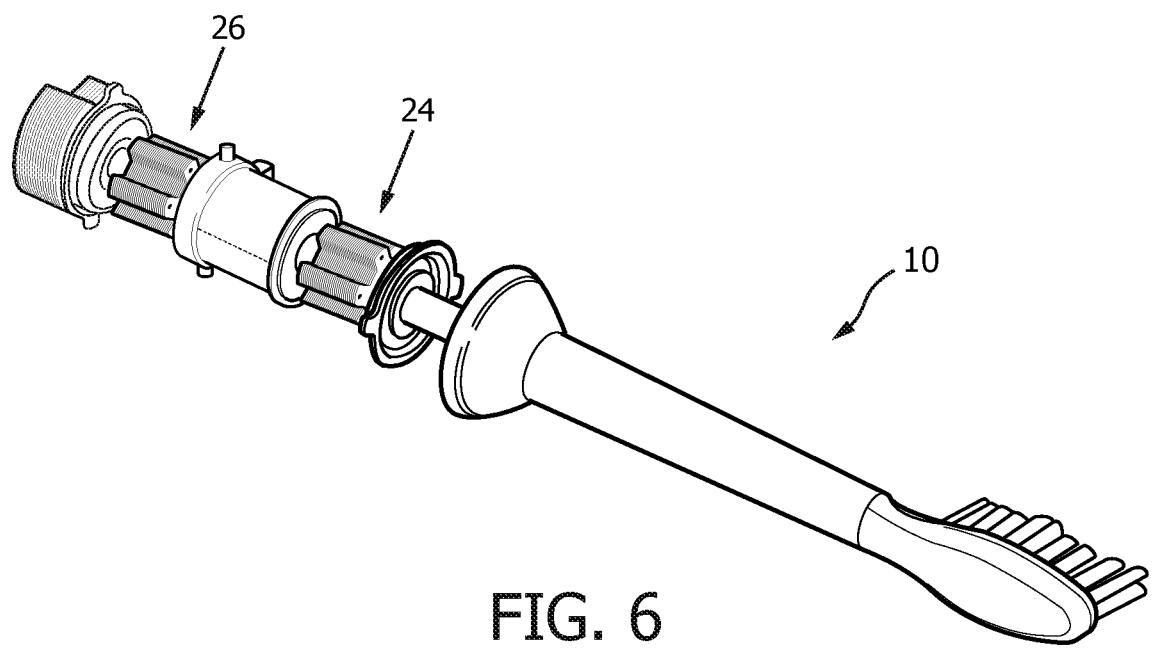
FIG. 6 is a perspective schematic of a personal care appliance according to an embodiment.

As shown in FIG. 6, according to an embodiment, the eccentric core may further include a second group of pole members 26, extending radially from a different portion of the spindle (i.e., separated by a length along the spindle from the first pole assembly 24).

Figure 7:
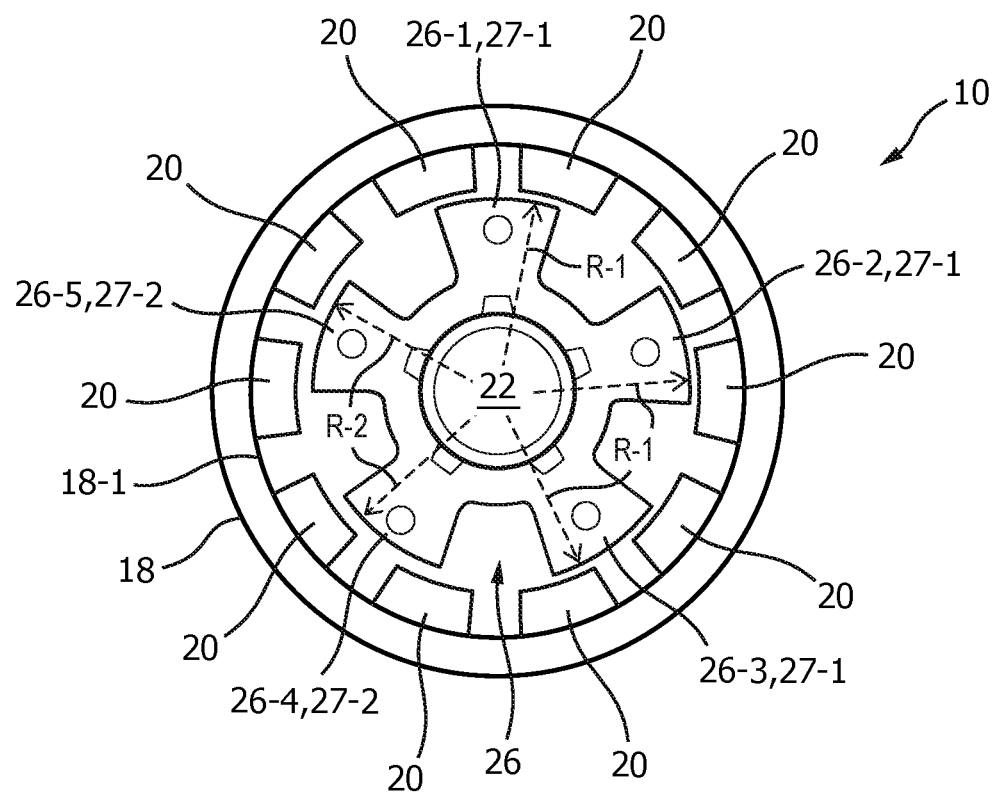
FIG. 7 is a cross-sectional view of a personal care appliance taken along "A-A" of FIG. 1 according to an additional embodiment.

As shown in FIG. 7, according to an embodiment, a second group of pole members/pole assembly 26 may be divided into at least two sets of pole members: 27-1, 27-2. The pole members of each set 27-1 (26-1, 26-2, 26-3), 27-2 (26-4 and 26-5), may have a set of lengths (distance from the center of spindle 22 to the farthest radial edge of a particular pole member), such that the average lengths of set 27-1 are greater than the average lengths of set 27-2. In other words, the pole members of set 27-1 can each have a average length larger than the average length of each pole member in set 27-2. In an exemplary embodiment, the second group of pole members 26 may be configured in the same manner as the first group of pole members to further preload the spindle. Stated differently, sets 25-1 and 27-1 and sets 25-2 and 27-2, respectively, may extend in the same direction and/or at the same length from the spindle 22. In an alternative embodiment, the second group of pole members 26 may have a different number of pole members, or may have pole members with different lengths than the first pole assembly 24, to generate a preload in a different direction than the first pole assembly 24 or to generate a stronger or weaker preload than the first pole assembly 24.

Referring again to FIG. 3, according to another embodiment, spindle 22 may be disposed within housing 18 via a set of bearings 28. Bearings 28 may have a centerline A3, which is mechanically offset from the principal axis A1, such that the spindle is positioned along secondary axis A2 due to this mechanical offset. Centerline A3 represents the midpoint of the bearing's core diameter. Although FIG. 3 depicts bearings centerline A3 overlaying the secondary axis A2, one of ordinary skill in the art will readily recognize that due to gaps between the bearings 28 and the spindle 22, secondary axis A2 may be offset from bearing centerline A3. Because spindle 22 is disposed along an axis offset from the primary axis, pole members of first pole assembly 24 along one side of spindle 22 will have a smaller magnet gap than the other. The pole members of first pole assembly 24 (which may or may not have varying lengths in this embodiment) with a smaller magnet gap caused by this mechanical offset will experience greater magnetic attraction, preloading spindle 22 and creating an asymmetrical magnet gap.

Bearings 28 may include (but are not limited to) any common bearings such as bushing bearings, sleeve bearings, ball bearings, or roller bearings. In one embodiment, bearings 28 are bushing bearings.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of."

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

What is claimed is:

1. An actuator for an electric toothbrush, comprising:
   a housing having an inner surface and a principal axis extending longitudinally through the center of the housing, and having a sequence of more than one magnet, disposed along the inner surface of the housing; and
   an eccentric core, comprising:
      a spindle of magnetizable material extending along a secondary axis, and
      a first pole assembly, arranged in a radial configuration about the spindle, and comprising a first set of pole members comprising at least one pole member extending radially at least a first average distance from the spindle, and a second set of pole members comprising at least one pole member extending radially a second average distance from the spindle, wherein the length of the first average distance is greater than the length of the second average distance such that the spindle is subjected to a bias force in a bias direction, radially from the principal axis, whereby the secondary axis is offset from the principal axis.

2. The actuator of claim 1, wherein the first set of pole members comprises more pole members than said second set of pole members.

3. The actuator of claim 2, wherein the first set of pole members comprises three consecutive pole members and the second set of pole members comprises two consecutive pole members.

4. The actuator of claim 1, wherein the first set further comprises at least one pole member extending radially farther than the remainder of the pole members in the first set.

5. The actuator of claim 1, further comprising:
   an output mounting shaft coupled to the housing and exhibiting a force in a radial direction (F1) upon the spindle when in use, wherein the bias direction (F2') is substantially opposed to the radial direction.

6. The actuator of claim 1, further comprising:
   an output mounting shaft coupled to the housing and exhibiting a force in a radial direction (F1) upon the spindle when in use, wherein the bias direction (F2) is in substantially the same as the radial direction.

7. The actuator of claim 1, wherein the eccentric core further comprises:
   a second pole assembly, arranged in a radial configuration about the spindle, and comprising a third set of pole members comprising at least one pole member extending radially a third average distance from the spindle, and a fourth set of pole members comprising at least one pole member extending radially a fourth average distance from the spindle, wherein the length of the third average distance is greater than the length of the fourth average distance.

8. An electric toothbrush having an actuator according to claim 1.

* * * * *